United States Patent [19]

De Oliveira

[11] Patent Number: 5,217,711
[45] Date of Patent: Jun. 8, 1993

[54] HAIR CARE SYSTEM

[76] Inventor: Mariana De Oliveira, 788 Adelaide St. West, Toronto, Ontario M6J 1B4, Canada

[21] Appl. No.: 777,733

[22] Filed: Oct. 16, 1991

[51] Int. Cl.$^5$ .......................... A61K 7/06; A61K 35/78
[52] U.S. Cl. ........................................ 424/70; 424/74; 424/195.1; 424/71; 514/880; 514/881
[58] Field of Search .................. 424/70, 71, 74, 195.1; 514/880, 881, 783

[56] References Cited

U.S. PATENT DOCUMENTS

| | | | |
|---|---|---|---|
| 3,824,304 | 7/1974 | Villanevia | 424/74 |
| 3,968,146 | 7/1976 | Lewis | 428/386 |
| 4,511,555 | 4/1985 | Faust | 424/74 |
| 4,659,566 | 4/1987 | Petrow | 424/71 |
| 4,861,593 | 8/1989 | Spearmon | 424/74 |
| 4,883,659 | 11/1989 | Goodman | 514/938 |
| 4,938,953 | 7/1990 | Pena | 424/70 |
| 4,999,195 | 3/1991 | Hayes | 514/880 |
| 5,081,151 | 1/1992 | Davis | 514/880 |

Primary Examiner—Thurman K. Page
Assistant Examiner—Sally Gardner
Attorney, Agent, or Firm—Eugene J. A. Gierczak

[57] ABSTRACT

In a composition for enhancing the growth of hair comprising a conditioner having the following ingredients based on a total of 500 grams by weight:

| | | |
|---|---|---|
| water | approximately | 435.5 gm. |
| cetyl alcohol | approximately | 12.5 gm. |
| standamul | approximately | 12.5 gm. |
| proteins | approximately | 35.0 gm. |
| citric acid | approximately | 2.5 gm. |
| honey | approximately | 0.5 gm. |
| wheat germ oil | approximately | 0.5 gm. |
| lecithin | approximately | 0.5 gm. |
| herbal extract | approximately | 0.5 gm. |
| methylchloroisothiazolinone | approximately | 0.5 gm. |

The composition also includes a shampoo and a cleansing solution.

5 Claims, No Drawings

HAIR CARE SYSTEM

FIELD OF THE INVENTION

This invention relates to a composition for treating human scalp and hair and particularly relates to a process for enhancing the growth of hair.

BACKGROUND OF THE INVENTION

The aging process as well as heredity have been long known to contribute to hair loss. In particular, the aging process tends to deplete the production of moisturizing agents such as natural human oils as well as cause the loss of hair growth.

Various attempts have heretofore been employed in order to strengthen hair growth or structure, moisturize the scalp, and minimize the loss of hair growth.

For example, U.S. Pat. No. 321,487 relates to a hair restorative and in particular consists of lime, plumbago, borax, bees wax, tallow, salt and lac sulphur.

Moreover, U.S. Pat. No. 3,168,538 teaches novel compounds and methods of producing sulphinate surface active agents which can be employed in cosmetic preparations and particular in a variety of shampoo formulations due to their high foaming. Yet another shampoo composition is disclosed in U.S. Pat. No. 3,267,039 which consists essentially of treithylonolamine lauryl sulphate in the range from 5% to 25% by weight.

Moreover U.S. Pat. No. 4,946,678 relates to a process of treating human scalp and hair composition comprising the steps of:

(a) applying a sanitizing agent to the balding area of the scalp to open and sanitize the pores and hair follicles of the scalp;

(b) applying heat and a soft agent to soften and separate sebum deposits in the pores and follicles of the scalp once they have been opened by the application of the sanitizing agent;

(c) then rinsing the scalp to remove deposits and agent previously applied thereto; and (d) then applying chalaza mixture to the scalp to nourish the roots and papillae of the hair in the scalp.

Finally, U.S. Pat. No. 5,017,368 relates to composition for application to hair or scalp which comprises at least one compound selected from the group consisting of forskolin and derivatives thereof and peptide.

These and other compositions have a limited utility.

It is an object of this invention to utilize and improve compositions for treating human scalp and hair compositions.

The broadest aspect of this invention relates to a composition for enhancing the growth of hair comprising a conditioner having the following ingredients based on a total of 500 grams by weight:

| | |
|---|---|
| water | approximately 435.5 gm. |
| cetyl alcohol | approximately 12.5 gm. |
| Standamul 100ZK (generically known as cetearyl alcohol (and) PEG-40 hydrogenated caster oil (and) stearalkonium chloride) | approximately 12.5 gm. |
| proteins | approximately 35.0 gm. |
| citric acid | approximately 2.5 gm. |
| honey | approximately 0.5 gm. |
| wheat germ oil | approximately 0.5 gm. |
| lecithin | approximately 0.5 gm. |
| herbal extract | approximately 0.5 gm. |
| methylchloroisothiazolinone | approximately 0.5 gm. |

It is another aspect of this invention to comprise a composition consisting of the combination of the conditioner as outlined above plus a shampoo comprising the following ingredients based on a total of 500 grams weight:

| | |
|---|---|
| water | approximately 257.5 gm. |
| sodium lauryl ether sulfate | approximately 200.0 gm. |
| cocamidopropyl betaine | approximately 10.0 gm. |
| cocamide DEA | approximately 10.0 gm. |
| sodium laureth sulfate and a pearlizing agent | approximately 5.0 gm. |
| citric acid | approximately 2.5 gm. |
| proteins | approximately 2.5 gm. |
| honey | approximately 0.5 gm. |
| wheat germ oil | approximately 0.5 gm. |
| lecithin | approximately 0.5 gm. |
| FD&C blue #1 | approximately Q.S. |
| FD&C yellow #5 | approximately Q.S. |
| methylchloroisothiazolinone | approximately 0.5 gm. |
| sodium chloride | approximately 10.0 gm. |

Another aspect of this invention comprises the composition of the combination of the conditioner and shampoo referred to above and a cleansing solution, said cleansing solution comprising the following ingredients in percentage by volume based on the volume of the total composition of said cleansing solution, namely:

| | |
|---|---|
| sodium iodide | approximately 3% |
| potassium iodide | approximately 1.5% |
| sodium thiosulphate | approximately .032% |
| alcohol with water base | 70% alcohol sufficient for the remainder |

Finally, it is another aspect of this invention to provide a process of treating human scalp and hair comprising the steps of:

(a) applying a shampoo to said hair and scalp and massaging the scalp for a period of at least 5 minutes, said shampoo comprising the following ingredients based on a total of 500 grams weight:

| | |
|---|---|
| water | approximately 257.5 gm. |
| sodium lauryl ether sulfate | approximately 200.0 gm. |
| cocamidopropyl betaine | approximately 10.0 gm. |
| cocamide DEA | approximately 10.0 gm. |
| sodium laureth sulfate and a pearlizing agent | approximately 5.0 gm. |
| citric acid | approximately 2.5 gm. |
| proteins | approximately 2.5 gm. |
| honey | approximately 0.5 gm. |
| wheat germ oil | approximately 0.5 gm. |
| lecithin | approximately 0.5 gm. |
| FD&C blue #1 | approximately Q.S. |
| FD&C yellow #5 | approximately Q.S. |
| methylchloroisothiazolinone | approximately 0.5 gm. |
| sodium chloride | approximately 10.0 gm. |

(b) removing said shampoo;

(c) then applying a conditioner and massaging the scalp for a period of at least 5 minutes, such conditioner comprising the following ingredients based on a total of 500 grams weight:

| | |
|---|---|
| water | approximately 435.0 gm. |
| cetyl alcohol | approximately 12.5 gm. |
| Standamul 100ZK (generically known as cetearyl alcohol (and) PEG-40 hydrogenated caster oil (and) stearalkonium chloride) | approximately 12.5 gm. |
| proteins | approximately 35.0 gm. |
| citric acid | approximately 2.5 gm. |
| honey | approximately 0.5 gm. |
| wheat germ oil | approximately 0.5 gm. |
| lecithin | approximately 0.5 gm. |
| herbal extract | approximately 0.5 gm. |
| methylchloroisothiazolinone | approximately 0.5 gm. |

(d) leaving the conditioner on said hair and scalp with a heating cap to permit the conditioner to penetrate into the pores of the scalp, for a period of approximately 20 minutes;

(e) rinsing said conditioner;

(f) applying a cleansing solution to said scalp for removing deposits of dead skin, said solution comprising the following ingredients in percentage by volume based on the volume of the total composition of said cleansing solution:

| | |
|---|---|
| sodium iodide | approximately 3% |
| potassium iodide | approximately 1.5% |
| sodium thiosulphate | approximately .032% |
| alcohol with water base | 70% alcohol sufficient for the remainder |

(g) leaving the cleansing solution on said scalp.

DETAILED DESCRIPTION OF THE INVENTION

It has been found that by utilizing a conditioner having the following composition, the hair of an individual tends to grow and thereby retarding the balding process as well as rejuvenating the growth of hair:

| | |
|---|---|
| water | approximately 435.0 gm. |
| cetyl alcohol | approximately 12.5 gm. |
| Standamul 100ZK | approximately 12.5 gm. |
| proteins | approximately 35.0 gm. |
| citric acid | approximately 2.5 gm. |
| honey | approximately 0.5 gm. |
| wheat germ oil | approximately 0.5 gm. |
| lecithin | approximately 0.5 gm. |
| herbal extract | approximately 0.5 gm. |
| methylchloroisothiazolinone | approximately 0.5 gm. |

Moreover, the protein utilized in the conditioner comprises of a milk amino acid.

It is the conditioner which apparently encourages the growth of hair.

However, it has also been found that by utilizing the combination of the conditioner as outlined above with shampoo having the following formulation that the growth of hair is further improved, namely:

| | |
|---|---|
| water | approximately 257.5 gm. |
| sodium lauryl ether sulfate | approximately 200.0 gm. |
| cocamidopropyl betaine | approximately 10.0 gm. |
| cocamide DEA | approximately 10.0 gm. |
| sodium laureth sulfate and a pearlizing agent | approximately 5.0 gm. |
| citric acid | approximately 2.5 gm. |
| proteins | approximately 2.5 gm. |
| honey | approximately 0.5 gm. |
| wheat germ oil | approximately 0.5 gm. |
| lecithin | approximately 0.5 gm. |
| FD&C blue #1 | approximately Q.S. |
| FD&C yellow #5 | approximately Q.S. |
| methylchloroisothiazolinone | approximately 0.5 gm. |
| sodium chloride | approximately 10.0 gm. |

It has been found that good results are observed by utilizing glycol disterate and cocamide DEA as the pearlizing agent. Furthermore, the protein used in the shampoo comprises also milk amino acids.

Furthermore, by utilizing the composition and formula of the conditioner and shampoo once a day, good results are observed in the growth of hair in balding areas.

Moreover, it has been found that the hair treatment system described heretofore is somewhat improved by utilizing a cleansing solution having the following ingredients in percentage by volume based on the volume of the total composition of the cleansing solution, namely:

| | |
|---|---|
| sodium iodide | approximately 3% |
| potassium iodide | approximately 1.5% |
| sodium thiosulphate | approximately .032% |
| alcohol with water base | 70% alcohol sufficient for the remainder |

The cleansing solution is utilized to keep the scalp clean and to remove dead skin. Good results are observed by using the cleansing solution three times a day.

The cleansing solution cleans the scalp while the formulation of the conditioner and shampoo moisturizes and enhances the growth of hair.

Moreover the letters Q.S. indicate quantum sufficient or mean "enough".

It has been found that good results are achieved in treating the human scalp and hair by utilizing the compositions referred to above and in particular by the steps of:

(a) applying the shampoo referred to above to the hair and scalp and massaging the scalp and hair for a period of at least 5 minutes;

(b) rinsing the shampoo;

(c) applying the conditioner with the formulation referred to above and massaging the scalp for a period of at least 5 minutes;

(d) leaving the conditioner on said hair and scalp with a heating cap to permit the conditioner to penetrate into the pores of the scalp for a period of approximately 20 minutes;

(e) rinsing the conditioner; and (f) then applying the cleansing solution referred to above to the scalp for removing deposits of dead skin having the formulation described herein; and (g) leaving the cleansing solution on said scalp.

Although the preferred embodiment as well as the operation and use have been specifically described, it should be understood that variations in the preferred embodiment could be achieved by a person skilled in the art without departing from the spirit of the invention.

The embodiments of the invention in which an exclusive property or privilege is claimed are defined as follows:

1. In a composition for enhancing the growth of hair comprising a conditioner having the following ingredients based on a total of 500 grams by weight:

| | | |
|---|---|---|
| water | approximately | 435.0 gm. |
| cetyl alcohol | approximately | 12.5 gm. |
| cetearyl alcohol (and) PEG-40 hydrogenated caster oil (and) stearalkonium chloride | approximately | 12.5 gm. |
| milk amino acids | approximately | 35.0 gm. |
| citric acid | approximately | 2.5 gm. |
| honey | approximately | 0.5 gm. |
| wheat germ oil | approximately | 0.5 gm. |
| lecithin | approximately | 0.5 gm. |
| herbal extract | approximately | 0.5 gm. |
| methylchloroisothiazolinone | approximately | 0.5 gm. |

2. In a composition as claimed in claim 1 wherein said protein comprises milk amino acids.

3. In a composition as claimed in claim 1 further including a shampoo acting in combination with said conditioner, said shampoo comprising the following ingredients based on a total weight of 500 grams:

| | |
|---|---|
| water | approximately 257.5 gm. |
| sodium lauryl ether sulfate | approximately 200.0 gm. |
| cocamidopropyl betaine | approximately 10.0 gm. |
| cocamide DEA | approximately 10.0 gm. |
| sodium laureth sulfate and a pearlizing agent | approximately 5.0 gm. |
| citric acid | approximately 2.5 gm. |
| milk aminoacids | approximately 2.5 gm. |
| honey | approximately 0.5 gm. |
| wheat germ oil | approximately 0.5 gm. |
| lecithin | approximately 0.5 gm. |
| FD&C blue #1 | approximately Q.S. |
| FD&C yellow #5 | approximately Q.S. |
| methylchloroisothiazolinone | approximately 0.5 gm. |
| sodium chloride | approximately 10.0 gm. |

4. In a composition as claimed in claim 3 wherein said pearlizing agent comprises glycol distearate and cocamide DEA.

5. In a composition as claimed in claim 4 further including a cleansing solution comprising the following ingredients in percentage by volume based on the volume of the cleansing solution:

| | |
|---|---|
| sodium iodide | approximately 3% |
| potassium iodide | approximately 1.5% |
| sodium thiosulphate | approximately .032% |
| alcohol/water base | 70% alcohol Q.S. 100% |

* * * * *